US011351258B2

(12) United States Patent
Ngwa

(10) Patent No.: US 11,351,258 B2
(45) Date of Patent: Jun. 7, 2022

(54) SYSTEMS, METHODS, AND BIOMATERIALS FOR RADIATION THERAPY

(71) Applicant: The Brigham and Women's Hospital, Inc., Boston, MA (US)

(72) Inventor: Wilfred F. Ngwa, Framingham, MA (US)

(73) Assignee: The Brigham and Women's Hospital, Inc, Boston, MA (US)

( * ) Notice: Subject to any disclaimer, the term of this patent is extended or adjusted under 35 U.S.C. 154(b) by 85 days.

(21) Appl. No.: 16/090,315

(22) PCT Filed: Apr. 3, 2017

(86) PCT No.: PCT/US2017/025728
§ 371 (c)(1),
(2) Date: Oct. 1, 2018

(87) PCT Pub. No.: WO2017/173440
PCT Pub. Date: Oct. 5, 2017

(65) Prior Publication Data
US 2019/0111134 A1 Apr. 18, 2019

Related U.S. Application Data

(60) Provisional application No. 62/316,831, filed on Apr. 1, 2016.

(51) Int. Cl.
*A61K 41/00* (2020.01)
*A61K 47/69* (2017.01)
*A61N 5/00* (2006.01)
*A61P 35/00* (2006.01)
*A61N 5/10* (2006.01)

(52) U.S. Cl.
CPC ...... *A61K 41/0038* (2013.01); *A61K 41/0057* (2013.01); *A61K 47/6929* (2017.08); *A61N 5/00* (2013.01); *A61N 5/1001* (2013.01); *A61P 35/00* (2018.01); *A61N 2005/1098* (2013.01)

(58) Field of Classification Search
None
See application file for complete search history.

(56) References Cited

U.S. PATENT DOCUMENTS

| 4,702,228 A | 10/1987 | Russel et al. |
| 6,107,102 A | 8/2000 | Ferrari et al. |
| 2007/0218006 A1 | 9/2007 | Norfray et al. |
| 2008/0177179 A1 | 7/2008 | Stubbs et al. |
| 2009/0186060 A1 | 7/2009 | Hainfeld et al. |
| 2012/0282185 A1* | 11/2012 | Dobson .............. A61K 33/24 424/9.42 |
| 2013/0158336 A1 | 6/2013 | Bensaoula et al. |
| 2013/0225901 A1 | 8/2013 | Krishan et al. |
| 2016/0016009 A1 | 1/2016 | Manzke et al. |

FOREIGN PATENT DOCUMENTS

| WO | 2015183346 A2 | 3/2015 |
| WO | 2017173440 A | 5/2017 |

OTHER PUBLICATIONS

Kotagiri et al. Breaking the depth dependency of phototherapy with Cerenkov radiation and low-radiance-responsive nanophotosensitizers. 2015 Nat. Nanotechnol. 10: 370-379. Epub Mar. 9, 2015. (Year: 2015).*
Hu et al. PET and NIR optical imaging using self-illuminating (64)Cu-doped chelator-free gold nanoclusters. 2014 Biomaterials 35: 9868-9876. (Year: 2014).*
Glaser et al., Optical dosimetry of radiotherapy beams using Cerenkov radiation: the relationship between light emission and does, Jul. 21, 2014, p. 3789-3811, vol. 59:14.
International Search Report and Written Opinion, dated Sep. 1, 2017, 29 pages.
Brown et al. "Towards photon radiotherapy treatment planning with high Z nanoparticle radiosensitisation agents: the Relative Biological Effective Dose (RBED) framework," Cancer Nanotechnol 2018; 9(1):9.
Roeske et al. "Characterization of the theoretical radiation dose enhancement from nanoparticles," Technol Cancer Res Treat. Oct. 2007; 6(5):395-401.

* cited by examiner

Primary Examiner — Jennifer Lamberski
(74) Attorney, Agent, or Firm — Quarles & Brady LLP

(57) ABSTRACT

Methods and systems for radiation therapy involve administering a payload/combination of biocompatible high-Z and semiconductor NPs to tissue, such as a tumor or an eye. Ionizing radiation may be directed towards the payload, and ionized electrons generate Cerenkov radiation (CR). The CR interacts with semiconductor NPs to produce chemical species that are damaging to cells. The payload may be administered via injection or via a radiotherapy (RT) device that includes NPs in a biodegradable polymer matrix. Biodegradation of the polymer matrix, which results in release of its payload, may be remotely activated using, for example, electromagnetic or sound waves. The payload may include one or more immunologic adjuvants capable of promoting an immunologic response at remote sites (such as a metastatic tumors) that are separate from the site at which the NPs and adjuvants were administered.

25 Claims, 10 Drawing Sheets

SYSTEMS, METHODS, AND BIOMATERIALS FOR RADIATION THERAPY

CROSS-REFERENCE TO RELATED APPLICATIONS

This application represents the national stage entry of International Application PCT/US2017/025728, filed Apr. 3, 2017, which claims the benefit of U.S. Provisional Application 62/316,831, filed Apr. 1, 2016. The contents of both applications are hereby incorporated by reference as set forth in their entirety herein.

This application is based on, claims priority to, and incorporates herein by reference in its entirety U.S. Provisional Application Ser. No. 62/316,831, filed Apr. 1, 2016, and entitled, "Smart Radiotherapy." The references cited in the above provisional patent application are also hereby incorporated by reference.

STATEMENT REGARDING FEDERALLY SPONSORED RESEARCH

This invention was made with government support under NIH/NCI 1 K01 CA172478-01 awarded by the National Institutes of Health. The government has certain rights in the invention.

FIELD OF THE INVENTION

This document concerns an invention relating generally to radiation therapy (radiotherapy), and more specifically, to methods, systems, and biomaterials capable of leveraging Cerenkov radiation to boost radiotherapy dose/damage to tissue.

BACKGROUND

Cancer is a leading cause of death worldwide, with over 14 million new cases diagnosed each year. In the United States, one in three persons is diagnosed with cancer in his or her lifetime. The World Health Organization estimates the number of cancer cases will grow to about 25 million per year by 2030. In addition to the severe human suffering it inflicts, cancer imposes an enormous global economic burden, at over US $2 trillion per year.

Currently, radiation therapy (radiotherapy) is used in the treatment of most cancer patients, either by itself or in combination with other treatment approaches such as surgery and chemotherapy. Radiation therapy is a treatment technique that delivers ionizing radiation to a defined target volume in a patient. Conventional external beam radiation therapy, also referred to as "teletherapy," is commonly administered by directing a linear accelerator ("linac"), or cobalt-60 ($^{60}$Co) teletherapy unit, to produce beams of ionizing radiation that irradiate the defined target volume in a patient. The radiation beam is a beam of radiation that may be delivered to the target region from several different directions, or beam paths. Alternatively, in brachytherapy, x-ray-emitting radioisotopes (in the form of metallic seeds) may be implanted into tissue to be treated.

Preferably, radiation is delivered in such a manner that the surrounding healthy tissue does not receive radiation doses in excess of clinically acceptable tolerances. The likelihood and extent of damage to healthy cells tends to increase with the duration of treatment with radiation. Thus, there is a strong need for methods and systems that are able to increase damage to targeted (diseased) cells and/or reduce damage to healthy tissue.

SUMMARY OF THE PRESENT DISCLOSURE

Exemplary systems and methods for radiation therapy involve administering a payload/combination of biocompatible high atomic number (high-Z) nanoparticles (NPs) and semiconductor NPs to a tissue site of a subject, such as a tumor, the eye, etc. A first radiation may be directed at the site at which the payload was administered. A second radiation is generated via interaction of the high-Z NPs with the first radiation. Additionally, chemical species are generated via interaction of the semiconductor NPs with the second radiation. The chemical species are damaging to cells at the tissue site. The first radiation may be ionizing radiation delivered as, for example, x-rays, and the second radiation may be Cerenkov radiation. The high-Z NPs may emit electrons via photoelectric interaction with the first radiation, and the electrons may further damage cells at the tissue site. The Cerenkov radiation may be generated via interaction of the electrons with tissue of the subject. The first radiation may be applied via an external radiation source, or a local (internal) radiation source, such as an implanted x-ray emitting radioisotope.

In certain implementations, the combination of NPs may be administered via injection. In other implementations, the combination of NPs may be alternatively or additionally administered via a radiotherapy (RT) device, such as a coated fiducial marker, a spacer, a beacon, or an injectable gel. The RT device may include a polymer matrix that is biodegradable, such that the RT device releases at least a portion of its payload via biodegradation of the polymer matrix. Biodegradation of the polymer matrix may be remotely activated using, for example, electromagnetic or sound waves.

In various implementations, the payload may include one or more immunologic adjuvants capable of promoting an immunologic response to targeted cells. Advantageously, the response could reach remote sites (such as metastasized tumors) that are separate from the site at which the adjuvants were administered. The immunologic adjuvants may include, for example, monoclonal antibodies, cell surface receptor inhibitors, antigens from cancer cells, etc. The payload may alternatively or additionally include, for example, other pharmaceuticals that can work synergistically with the NPs and/or the immunologic adjuvants.

The disclosed methods and systems are able to leverage Cerenkov radiation in a potent approach that could substantially reduce treatment times for radiotherapy. Further advantages and features of the invention will be apparent from the remainder of this document in conjunction with the associated drawings.

The foregoing and other aspects and advantages of the invention will appear from the following description. In the description, reference is made to the accompanying drawings that form a part hereof, and in which there is shown by way of illustration preferred implementations of the invention. Such implementations do not necessarily represent the full scope of the invention. It is noted that the components depicted in the figures are not necessarily to scale.

DETAILED DESCRIPTION OF THE PRESENT DISCLOSURE

Cerenkov radiation (CR) is electromagnetic radiation (light) emission resulting when charged particles (such as electrons) travel through a dielectric medium faster than the phase velocity of light in the medium. CR has a broad-band spectrum with a large percentage falling in the ultraviolet region. Radiotherapy beams may produce CR within tissue, but the CR has limited penetration and by itself is relatively ineffective in radiation therapy.

Figure 1:
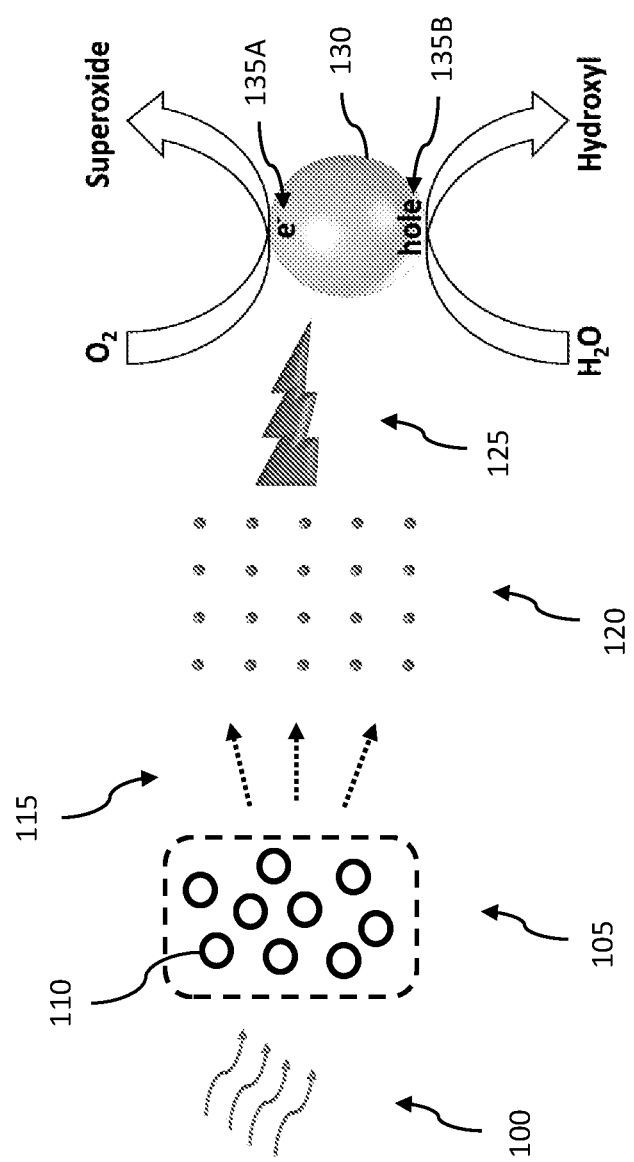
FIG. 1 depicts application of ionizing radiation, and interaction of resulting electrons with tissue to generate Cerenkov radiation (CR), which in turn excites production of reactive oxygen species (ROS), such as hydroxyl and superoxide radicals, on the surface of nanoparticles (NPs).

Referring to FIG. 1, a first radiation 100 (which may be ionizing electromagnetic radiation such as x-rays) may be directed at a tissue site 105, such as a tumor with cancerous cells or an eye. The tissue site 105 may include first nanoparticles (NPs) 110, such as high atomic number (high-Z) nanoparticles (e.g., gold NPs, gadolinium NPs, and iron oxide NPs), as further discussed below. Tissue at the tissue site 105, and/or the first NPs, receive the radiation 100 and release electrons 120 via the photoelectric effect or other ionization 115. Electrons 120 traveling through tissue with sufficient velocity will generate CR 125, which may be received by second NPs, such as semiconductor NPs at the tissue site 105 (e.g., titanium oxide, zinc oxide, etc.), as also discussed below. In certain implementations, the second NPs are titanium dioxide (titania), which is an inert semiconductor with a band gap of about 3 eV (electronvolts). After being excited by CR 125, titania can form electron-hole pairs (135A, 135B) and induce the production of reactive oxygen species (ROS), such as superoxide and hydroxyl. ROS are able to damage DNA and bring about cell death.

Figure 2B:
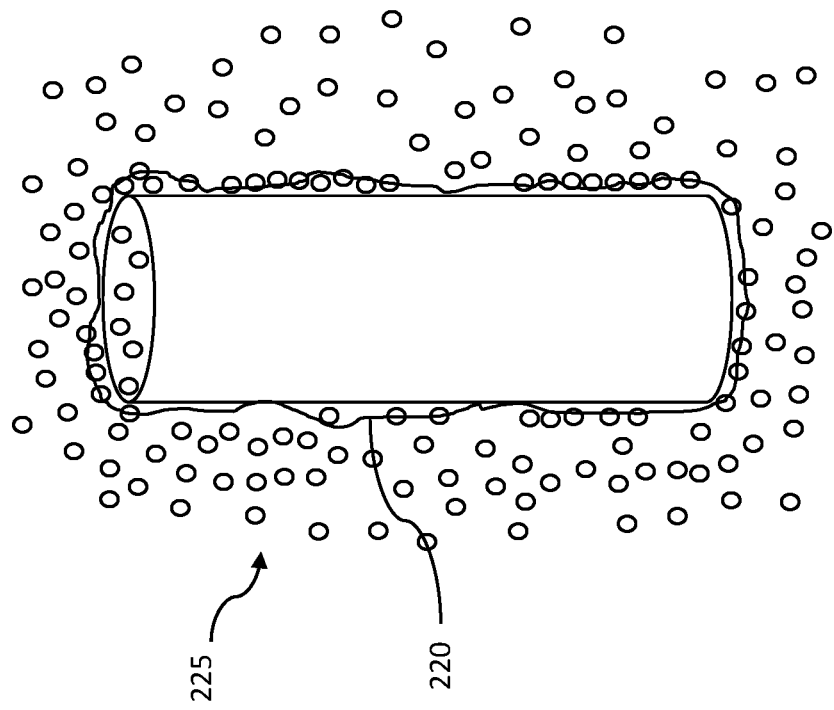
FIG. 2B depicts release of NPs in the RT device of FIG. 2A and diffusion of released NPs.
Figure 2A:
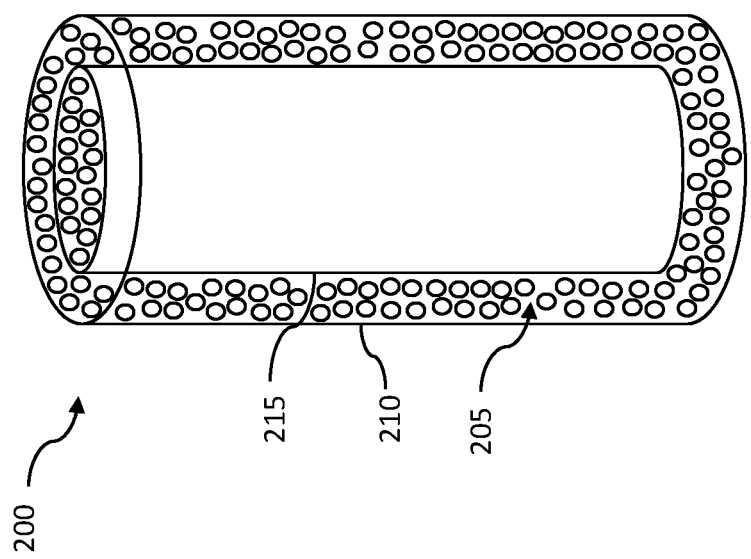
FIG. 2A depicts an exemplary radiotherapy (RT) device with a hollow core and NPs embedded in a biodegradable polymer matrix.

The NPs may be administered in multiple ways. Referring to FIG. 2A, in certain implementations, a "smart RT" device 200 can incorporate a potent payload 205 with, for example, a combination of high-Z NPs and semiconductor NPs. Concentrations of, for example, up to 7 mg/g high-Z could be employed in combination with semiconductor NPs of various concentrations shown to boost damage to cancer cells, such as concentrations discussed below in the context of the presented study. The payload 205 may be embedded in a polymer matrix 210 designed to contain a high concentration of NPs. The RT device 200 may include an RT biomaterial core 215, such as a fiducial marker, beacon, etc. To allow for increased payload sizes, the RT biomaterial 215 may be hollow. Referring to FIG. 2B, the polymer matrix 210 may be biodegradable, such that once the RT device 200 is in place (at the tissue site), the polymer matrix 210 may degrade 220. As the polymer matrix 210 degrades, the payload 205 may be eluted/released directly into the tissue (such as a tumor). The polymer matrix 210 may include, for example, PLGA (poly(lactic-co-glycolic acid)), chitosan, or other biocompatible polymers and blends thereof. Once released, the payload diffuses 225 into surrounding tissue. In other implementations, the combination of NPs may be directly administered at the tissue site. For example, the NPs may be delivered via intratumoral injection, if deemed appropriate. The injection may include an injectable gel containing the NPs. As will be further discussed, during radiotherapy, the NPs will significantly enhance local tumor cell kill, allowing for the primary dose to normal tissue to be minimized.

Thus, during radiotherapy, the high-Z nanoparticles can emit electrons due to the interaction of the radiotherapy photons (first radiation) with the high-Z nanoparticles (via, for example, the photoelectric effect). The emitted electrons can themselves amplify the damage to cancer cells. The emitted electrons from the high-Z NPs also in turn generate Cerenkov radiation. Because of the presence of the semiconductor NPs (such as titania or zinc oxide NPs), the Cerenkov radiation produces highly damaging ROS that further amplify the dose to the cancer cells, including typically radioresistant cells (i.e., cells that resist treatment by application of radiation). Hence the cancer cells are impacted in multiple ways, which allows for a substantial reduction of current typical radiotherapy treatment times and maximization, or at least a substantial enhancement, of therapeutic efficacy. Because the primary radiotherapy beam also generates Cerenkov radiation, this additional Cerenkov radiation can promote further generation of ROS and hence increase damage to targeted cells. Because the combination of these two types of NPs (i.e., high-Z and semiconductor) can substantially reduce radiotherapy treatment times, this approach can reduce wait times and increase the number of patients that can be treated in the clinic. This is particularly advantageous in resource-limited settings.

Figure 3:
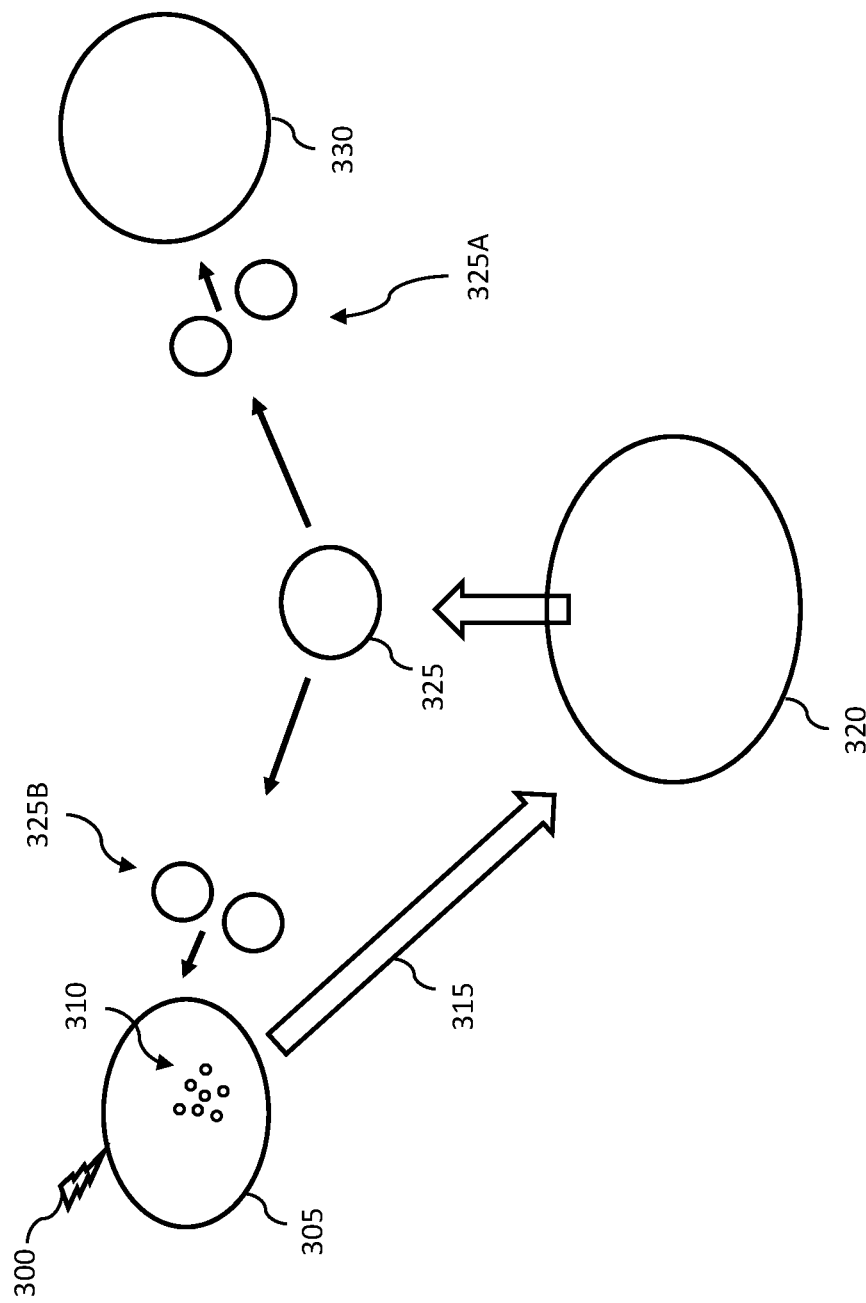
FIG. 3 depicts a process by which immunologic adjuvants (immunoadjuvants), which may be delivered to tissue via injection or via the payload of an RT device, promote an immune response to cells (such as those of a metastasized tumor) that are not co-located with cells at the tissue site at which the adjuvants were administered.

In certain implementations, the payload/NPs at the core of exemplary RT devices could further be functionalized with immunologic adjuvants. For cancer treatment, for example, such an approach could help prime the treatment of metastasized tumors, such that the radiotherapy process impacts not just irradiated sites, but remote sites that are not directly targeted with radiation. Referring to FIG. 3, radiation 300 is applied to tumor 305, which has had a payload of NPs and immunologic adjuvants 310 injected or implanted via a RT device. The immunologic adjuvants 310 may be carried by lymphatic vessels 315 to lymph node 320. Antigen presenting cells (APCs) in lymph node 320 help turn naïve CD8 cells into cytotoxic CD8 cells 325. CD8 cells 325A are able to attack and kill metastatic tumor 330 (without application of radiation at the remote sites), which may be spread to multiple sites in the patient. CD8 cells 325B could also attack the irradiated tumor 305.

Examples of potentially suitable adjuvants include, for example, granulocyte macrophage colony-stimulating factor (GM-CSF), anti-CD40 (cluster of differentiation 40), PD-1 (programmed cell death protein 1) path inhibitors, anti CTLA-4 (cytotoxic T-lymphocyte-associated protein 4) monoclonal antibodies, and other compounds approved by the U.S. Food and Drug Administration (FDA) to treat cancer or other targets.

Such a combination of NPs with immunologic adjuvants delivered/administered slowly in-situ can allow for treatment of metastatic disease and prevention of cancer recurrence. Such treatment of metastatic tumors greatly reduces systemic toxicity (by, for example, reducing or eliminating the need for radiotherapy, chemotherapy, etc.), which is a critical barrier/concern of conventional approaches. It is noted that the exemplary high-Z and semiconductor NPs are both relatively non-toxic by themselves, even if they escape into the blood stream. In addition to immunologic adjuvants, the RT device/payload/injection may also be provided with other compounds and synergistic pharmaceutical agents to further enhance outcomes of the treatment.

The rate and timing of the release of NPs (including immunologic adjuvants or other compounds added to the payload) can be tailored or otherwise controlled so as to achieve a desired outcome. For example, in exemplary implementations, the polymer weight or type can be customized to adjust the rate of biodegradation. This facilitates coordination of NP infusion with radiation therapy schedules. Because the payload may diffuse differently depending on the NPs/compounds and on the tissue through which the NPs diffuse, rate of polymer matrix biodegradation may be based at least in part on anticipated diffusion rate. Faster biodegradation may be desirable, for example, when diffusion times are expected to be higher, as the time for diffusion affects the distribution and concentration of NPs in the tissue that is to be irradiated. Similarly, if the delay between administration of NPs and irradiation is great, the polymer may be tailored to slow the rate of biodegradation so as to slow or delay the diffusion of NPs. In other implementations, the RT device may be configured to be remotely activated using, for example, sound or electromagnetic waves. For example, the polymer may be stimulated to begin biodegradation when needed or desired. The activation may be timed based on, for example, radiotherapy schedules.

Further advantages of exemplary RT devices include reduction of image artifacts due to the hollow core design. It has been shown that currently-used RT devices can cause image distortions as high as the distortion caused by solid metals. Using NPs in hollow core can provide contrast but reduce distortions, due to the small size of the NPs, around which electromagnetic waves are relatively less distorted.

Additionally, the semiconductor NPs could be doped with multimodal image contrast agents to enhance imaging during cancer treatment. Examples of such agents could be gadolinium nanoparticles which can provide magnetic resonance image (MRI) contrast and computerized tomography (CT) imaging contrast.

Advantageously, the NPs can be programmed to serve as an in-situ biosensor that can monitor treatment outcomes. Functionalized NPs could interact with analytes present in the tumor microenvironment, such as antigens generated during radiotherapy. That interaction could translate to electrochemical, electrochemiluminescent, magnetic, gravimetric, or optical signals, which can be detected by imaging. The NPs may be functionalized via, for example, attachment of antibodies (immunoadjuvants) or other bio/chemical molecules/compounds to the NPs.

In exemplary implementations, the NPs may have diameters varying from a few nanometers up to several microns, or other sizes as deemed suitable. The NPs may be formed, for example, to be spheres, rods, cubes, elliptical, or core-shell structures. Exemplary RT devices may be, for example, 3 to 5 mm in length, and 0.5 to 1.5 mm in diameter, although the RT devices can have other dimensions to suit different applications. The hollow core, and the dimensions thereof, can be adjusted to provide for varying concentrations and quantities in the payloads of NPs (and other compounds) to be administered.

Exemplary approaches disclosed herein provide for a potent combination of high-Z and semiconductor nanoparticles that can synergistically leverage both the photoelectric effect and Cerenkov radiation (which may be referred to as "double radiotherapy") to enhance damage to target cells during radiotherapy/radiosurgery. In exemplary implementations, RT devices can enable substantial reduction in radiotherapy treatment times for both external beam radiotherapy (using, for example, photons, electrons, protons, gamma-rays, etc.) as well as brachytherapy (that is, internal radiotherapy) in applying double radiotherapy to help maximize damage to diseased cells.

Exemplary methods and systems can be used to substantially enhance radiotherapy treatment of, for example, cancer, such as pancreatic cancer, lung cancer, breast cancer, prostate cancer, and other cancer sites (which may use RT biomaterials), with enhanced therapeutic efficacy. Moreover, exemplary implementations can be applied to treat other conditions and diseases with little or no modification. For example, the disclosed approach can be applied to treating macular degeneration, such as wet age-related macular degeneration (AMD) diseased cells. In such applications, a combination of NPs may be used without a polymer matrix because of the anatomy of the eye as compared with tumors. For example, with tumors, currently-used RT devices may be substituted with exemplary RT devices loaded with payloads as discussed here. For other diseases (such as ocular diseases), such RT devices may not be desired because of, for example, the anatomy or physiology of the targeted tissue site.

Advantageously, by simply replacing current inert RT devices like fiducials and spacers, exemplary RT devices disclosed here can be used with no additional clinical procedure or discomfort to patients. Consequently, given the direct delivery into the tumor sub-volume, implementing the approach being discussed would not involve added risk or inconvenience.

The discussion now turns to a study investigating the feasibility of exploiting the CR present during external beam radiotherapy (EBRT) for significant therapeutic gain, using titania NPs delivered via exemplary RT biomaterials. Monte Carlo radiation transport simulations have been used to calculate the total CR yield inside a tumor volume during EBRT compared to that of the radionuclides. Also considered is intratumoral titania delivery using RT devices (e.g., fiducials) loaded with NPs. The intratumoral distribution/ diffusion of titania released from the fiducials was calculated. To confirm the CR induced enhancement in EBRT experimentally, 6 MV radiation was used to irradiate human lung cancer cells with and without titania NPs, and clonogenic assays were performed. For a radiotherapy biomaterial loaded with 20 µg/g of 2-nm titania NPs, at least 1 µg/g could be delivered throughout a tumor sub-volume of 2-cm diameter after 14 days. This concentration level could inflict substantial damage to cancer cells during EBRT. The Monte Carlo results showed the CR yield by 6 MV radiation was higher than by the radionuclides of interest and hence greater damage may be obtained during EBRT. In-vitro study showed significant enhancement with 6 MV radiation and titania NPs. These findings demonstrate the approach of capitalizing on CR present during megavoltage EBRT to boost damage to cancer cells. Monte Carlo simulations show that the CR energy fluence is in the order of nJ/cm² for radionuclides, and mJ/cm² for radiotherapy beams. The greater CR present in EBRT could thus be leveraged to substantially amplify damage to cancer cells using titania NPs as a photosensitizer targeted at the tumor.

Methods for Monte Carlo simulation of CR production. Monte Carlo simulation was done using Geant4 for both external beam radiation and radionuclides in a water phantom. To facilitate this study, the Geant4 standard electromagnetic physics option 3 was used. Dose deposition by radiation sources and CR production spectra in the excitation range of titania (200-400 nm) were calculated.

Based on Eqns. (1) and (2), the CR production depends on charged particle energy and on the water refractive index:

$$\frac{dN}{dx} = 2\pi\alpha\left(1 - \frac{1}{\beta^2 n^2}\right)\left(\frac{1}{\lambda_1} - \frac{1}{\lambda_2}\right), \quad (1)$$

$$\beta = \sqrt{1 - \left(\frac{mc^2}{E + mc^2}\right)}. \quad (2)$$

Here, dN/dx is the production of CR per unit length of the electron track and a is the fine structure constant, 1/137. β is the relativistic phase velocity, which is given by equation (2). n is the water refractive index, and $\lambda_1$ and $\lambda_2$ are the CR wavelengths between which the calculations are performed. The energy-dependent refractive index of water was used as reported by Daimon and Masumura.

Note that there is an energy threshold for CR production, i.e., $$\frac{1}{\beta^2 n^2}$$

must be smaller than 1, which sets a lower limit (about 210 keV in water) for the incident radiation energy. During the simulation, to make sure that the cut-off energy of charged particles was lower than the CR production threshold, the gamma photon, electron and positron production cutoffs were set to 0.2 mm in water.

Geant4.10.1 was used to simulate ionizing radiation induced CR production in a 1 cm diameter spherical volume using two external radiotherapy phase-space sources: Varian Clinac IX 6 MV (10×10 cm²) and Eldorado ⁶⁰Co (10×10 cm²). The target volume was located in a cubic water phantom (40×40×40 cm³). The volume was placed at maximum dose depth for both cases: 1.5 cm for 6 MV source and 0.5 cm for ⁶⁰Co.

¹⁸F, ¹⁹²Ir and ⁶⁰Co were simulated using Geant4 radioactive decay models as internal sources. For ⁶⁰Co and ¹⁹²Ir, the sources were located in the center of scoring volume, whereas ¹⁸F was uniformly distributed in the volume to model clinical scenarios. Target volume was the same as that of external beam radiation.

Figure 4:
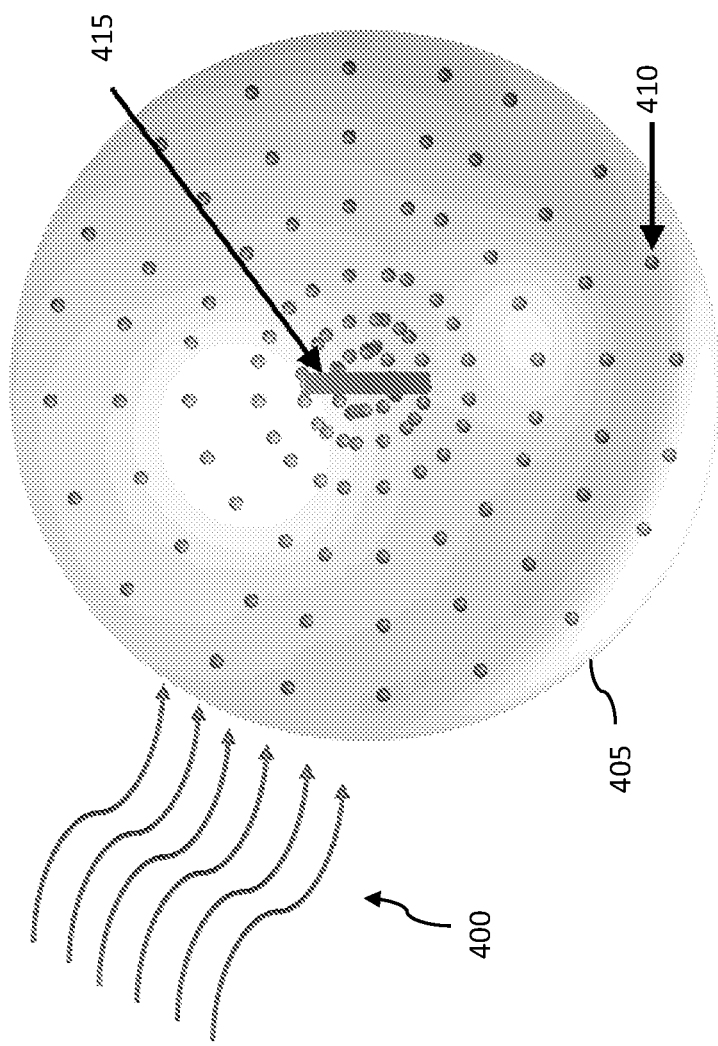
FIG. 4 depicts a model of diffusion of NPs (such as titanium oxide) from a RT device/biomaterial into tissue.

Methods for NP delivery modeling: A schematic of the radiotherapy biomaterials loaded with titania NPs for sustained in-situ release is shown in FIG. 4, which depicts radiation 400 irradiating tissue 405 (which may be a tumor). While the intratumoral biodistribution of the NPs 410 is relatively more complex, a diffusion model with a steady state isotropic release was adopted. NPs 410 diffuse directly into the tumor 405 over time from the radiotherapy biomaterial 415, assuming no NP present in tissue initially, via the following experimentally validated equation:

$$C(x, t) = C_s\left[1 - erf\left(\frac{x}{2\sqrt{Dt}}\right)\right]. \quad (3)$$

Here, $C_s$ is the initial NP concentration, defined at the surface of the new design radiotherapy biomaterial. C(x,t) is the final concentration at distance x and after diffusion time t. D is the diffusion coefficient with units cm²/s.

An in-vivo determined value, 2.2×10-8 cm²/s, has been published as the diffusion coefficient for 10 nm NPs. The Stokes-Einstein diffusion formula was used to estimate the D values for other sized NPs:

$$D = \frac{K_B T}{6\pi\eta r}. \quad (4)$$

In this equation, $K_B$ is the Boltzmann constant, T is the absolute temperature, η is the viscosity of medium, which was assumed constant, and r is the radius of spherical NPs.

The minimum concentration desired in each tumor voxel was 0.625 µg/g in order to achieve significant therapeutic gain. Initial concentration, $C_s$, was taken to be 20 µg/g, which has been shown to be relatively safe. A clinically relevant wait time, 14 days, was used for the evaluation.

Methods for in-vitro experiment: 5 nm anatase titania NPs (99.5% wt/wt) were purchased from US Research Materials, Inc. (Stock #: US3838). NP stock solution was made at 1 µg in 10 µL of sterile distilled water, and sonicated using an ultrasonic water bath for 20 minutes before treating the cells. A549 were purchased from ATCC and cultured in RPMI-1640 media supplemented with 10% FBS. Cells were incubated at 37° C. in a humidified atmosphere (5% CO₂, 95% air).

6 MV radiation was delivered using a Clinac TX machine at 100 cm SAD (source-to-axis distance) with 10 cm buildup and 5 cm backscatter (using solid water). The beam was delivered at gantry zero with a field size of 15×15 cm². Dose rate was set to be 400 MU (monitor units)/min with 121.5 MU/Gy.

500 A549 cells per well were seeded in 6-well plates on day one. 0.5 µg/g (NP per cell culture media) of NPs were treated to the cells on day three by replacing the regular cell media with NP-added media. Radiation was delivered on day four. Cell culture media were changed once 24 hours after irradiation and then biweekly. One week after irradiation, colonies were stained with crystal violet (1% by weight) and counted. Experiments were run in triplicates. Student's t-tests were performed using Mathematica.

Figure 5A:
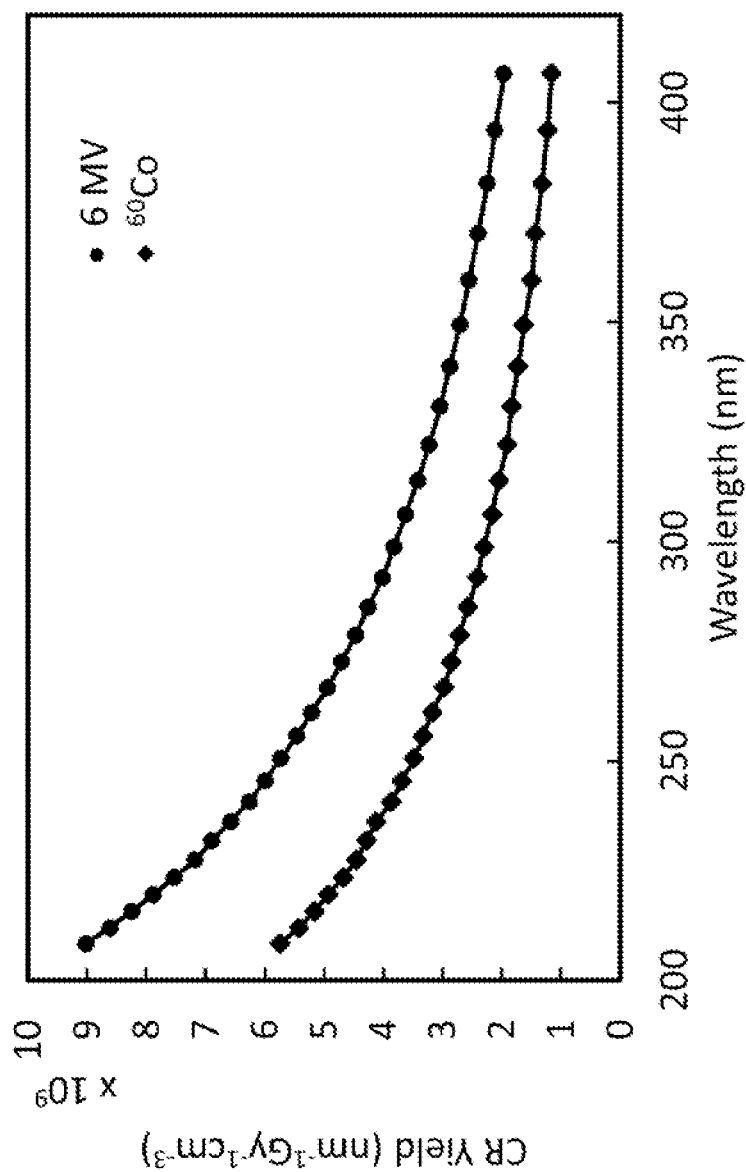
FIG. 5A represents CR production per unit dose deposition inside a target volume by external radiation sources: 6 MV (megavoltage) and $^{60}$Co.
Figure 5B:
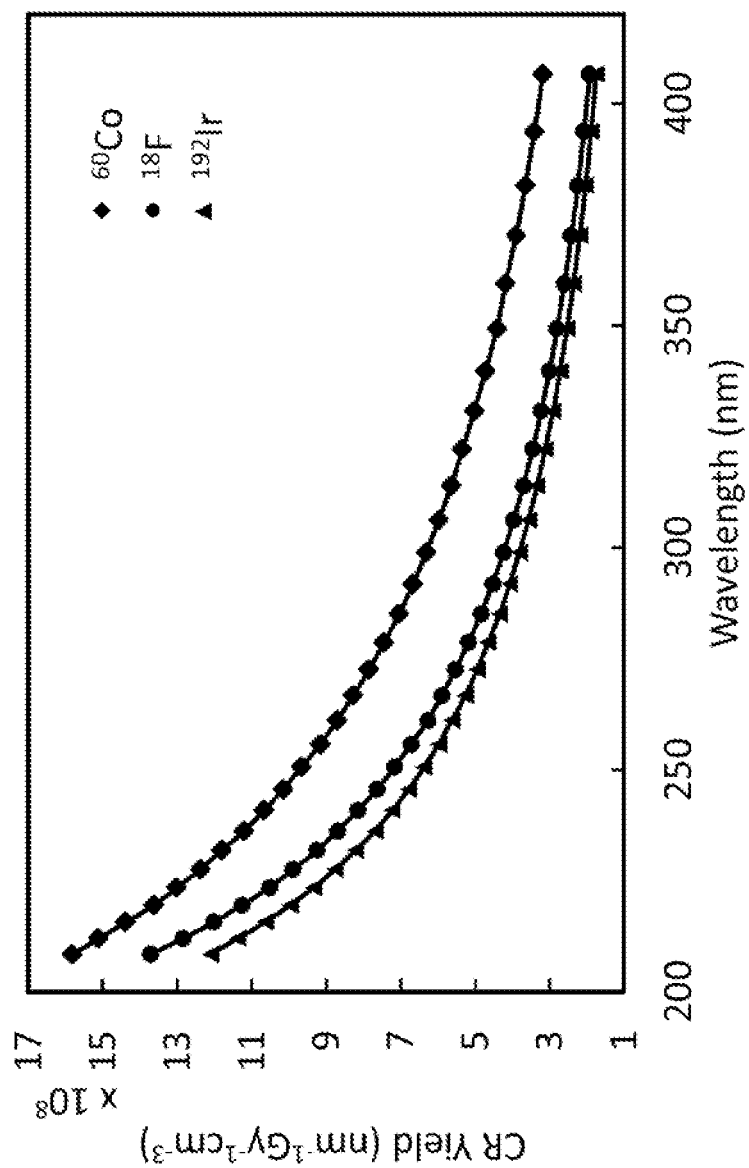
FIG. 5B represents CR production per unit dose deposition inside a target volume by internal radiation sources: $^{60}$Co, $^{18}$F, and $^{192}$Ir. It is noted that different source-target geometries were used in order to be close to clinical scenarios.

Results of Monte Carlo simulation of CR production. FIGS. 5A and 5B show the number of CR photons produced by different radiation sources. The simulation results were normalized by CR wavelength, tumor volume, and dose deposition. The results showed that 6 MV radiation produced the most CR per unit dose deposition: about 10 times higher than $^{18}$F. Overall, CR yield decreased as its wavelength increased. It is noted that $^{60}$Co was able to produce relatively high CR whether it was used as an external or an internal source.

Figure 6:
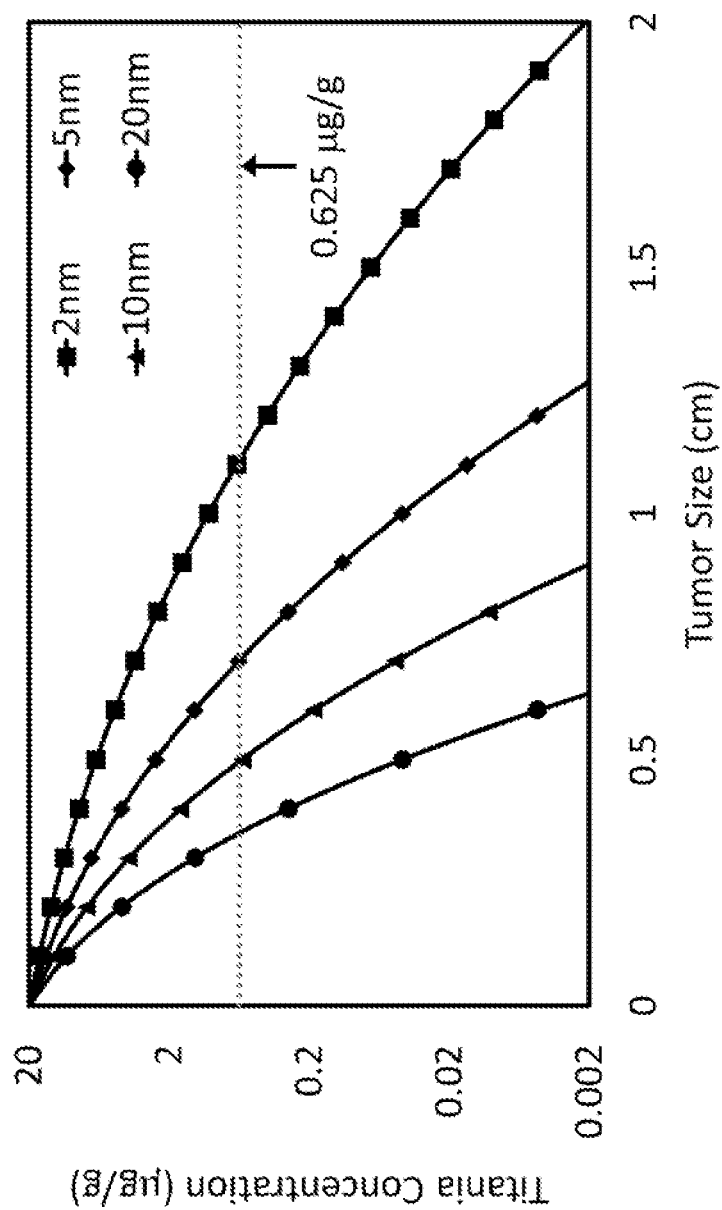
FIG. 6 represents titanium oxide (titania) concentration in tumor (radius ≤2 cm) after 14-day diffusion with 20 μg/g initial concentration. It is noted that different sized NPs can be used for different sized tumors.
Figure 7:
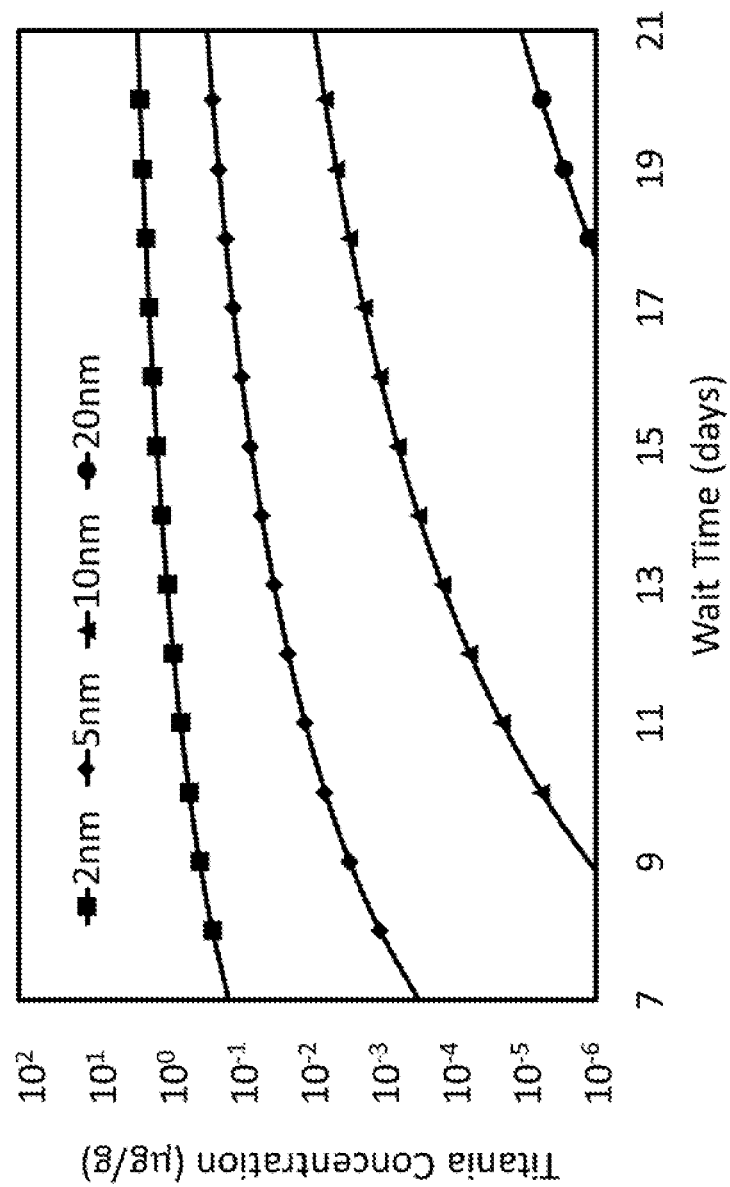
FIG. 7 represents the minimum concentration of titania in tumor (radius=1 cm) with up to 30-day diffusion and 20 μg/g initial concentration.

Results of NP delivery modeling. With a fixed diffusion time of 14 days, the needed/minimum titania concentration of 0.625 μg/g could be achieved at a distance of 1 cm for 2 nm titania. The diffusion distance corresponded to the tumor radius. The distance decreased with increase in nanoparticle size, as would be expected (FIG. 6). For a tumor sub-volume size of 1 cm diameter, the minimum concentration could be achieved for a range of titania sizes up to 20 nm. There was also interest in a particular tumor size (radius=1 cm), and the concentration profile over a range of time (7-21 days) was obtained, since the actual treatment schedule could vary among different clinics (FIG. 7). Altogether, these results showed the possibility of treatment optimization based on clinical schedule and tumor size.

Figure 8:
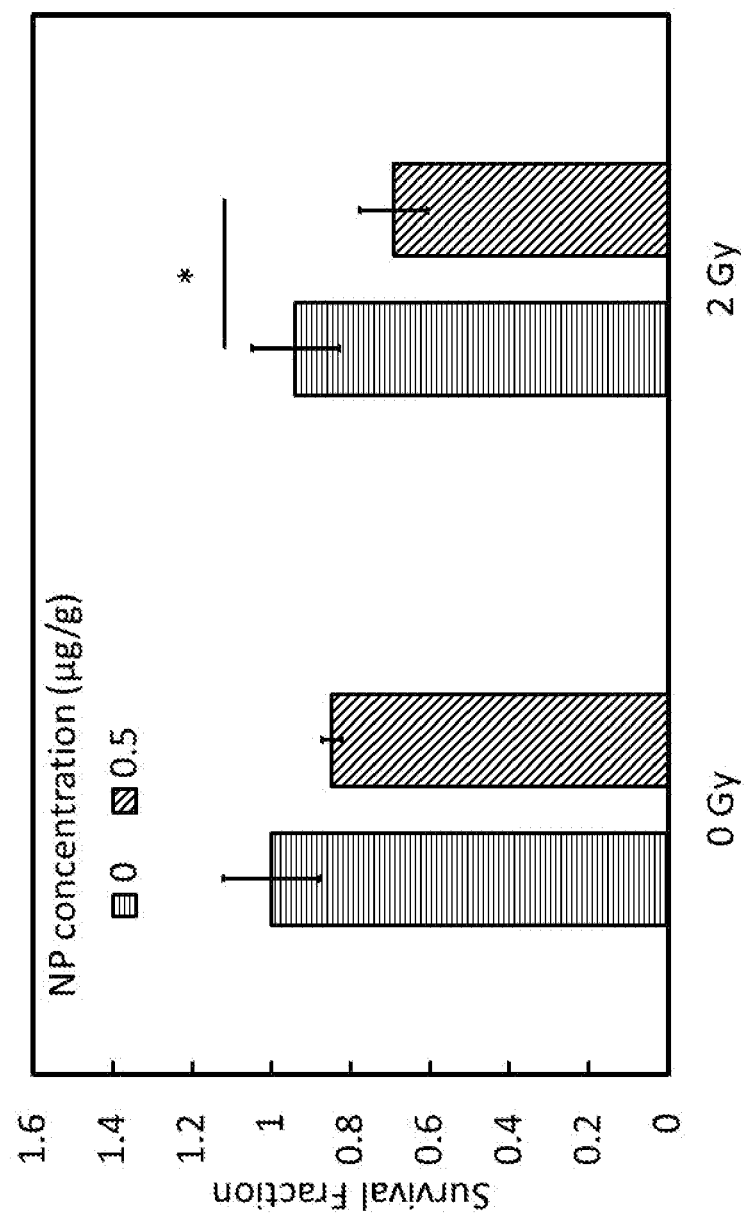
FIG. 8 represents A549 cell survival fraction with 2 Gy (gray) radiation and 0.5 μg/g of titania NPs; 6 MV radiation was delivered using a Clinac TX (*p<0.05). It is noted that groups with no radiation showed no significant difference, which meant titania NPs by themselves had no or little effect on cell survival fraction.

Results of in-vitro experiment. As shown in FIG. 8, adding titania NPs alone did not increase cancer cell killing significantly. When A549 cells were irradiated by 2 Gy of 6 MV radiation, cell survival remained almost the same as that of the control group. Synergistic effect for the combination of ionizing radiation and titania NPs was observed in the 6 MV experiments, where 20% more cancer cells were killed in the group with both radiation and 0.5 μg/g NPs, compared to that with radiation alone.

The Monte Carlo simulations show that much more CR is produced by MV radiation than by radionuclides. Therefore, more titania NPs can be excited and used for cancer cell killing. Clinically, more than one radiotherapy biomaterial loaded with titania can be used, which would result in enhanced tumor coverage. The typical number of radiotherapy biomaterials ranges from 2 to 5, although other numbers may be used as deemed suitable. Alternatively or additionally, a higher initial concentration may be used, which can accelerate the diffusion process.

Figure 9:
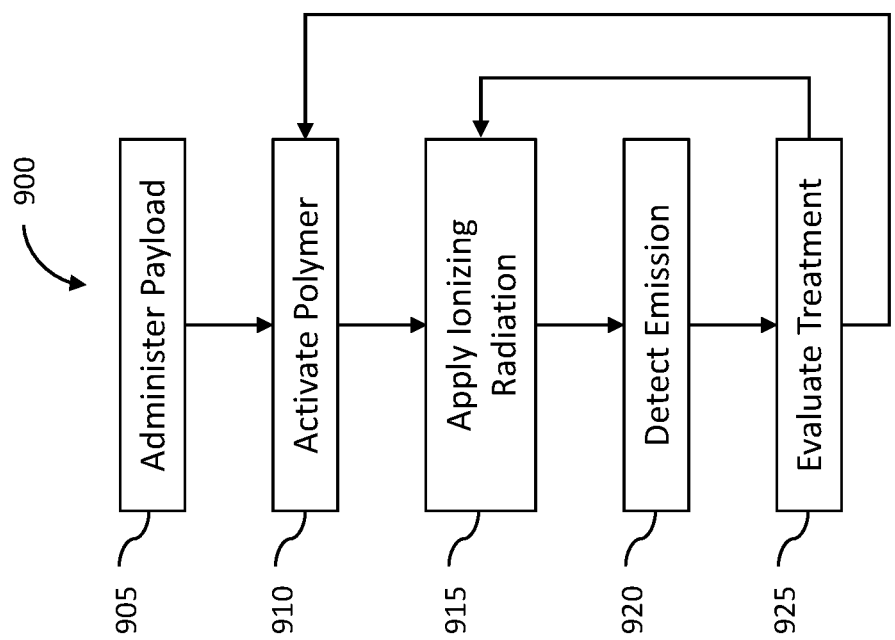
FIG. 9 provides an exemplary radiotherapy process involving the use of exemplary NP payloads.

Referring now to FIG. 9, an exemplary process 900 begins with administration of a payload 905 via, for example, injection or implantation of an RT device at a targeted tissue site, such as a tumor or an eye. The payload may include, for example, NPs and immunologic adjuvants in a biodegradable polymer matrix. If the polymer matrix can be activated remotely, a stimulator (such as a source of electromagnetic or sound waves) can be used to activate the polymer 910 to initiate or accelerate biodegradation. A certain amount of time may be allowed to pass, to allow for the release of the NPs and a certain amount of diffusion. The wait time may be based on, for example, the concentration of the NPs (the higher the concentration, the less time that may be needed), the size of the tumor (the larger the tumor, the more time that may be needed), the size and shape of the NPs (rounder, smaller NPs may diffuse more quickly than large cubes), etc.

Following the wait time, ionizing radiation (from an external or internal source) may be applied 915 to the site at which the payload was administered. A detector may be used to detect emissions at the tissue site 920, and the emissions correlated with a treatment outcome. The NP can be functionalized to interact with antigens generated by radiation. An imaging detector could image these interactions and correlate them to treatment outcomes. For example, more intense readings could be positively correlated with greater production of neoantigens or ROS, which would be expected to cause more damage to targeted cells. Following the evaluation, the same (or other polymer matrix of another RT device), which may not have been activated using the waves previously used for activating polymer, may be activated again using additional electromagnetic or sound waves 910. Alternatively or additionally, depending on the evaluation of treatment outcome, additional ionizing radiation may be applied. For example, in the above example, if readings do not indicate sufficient production of neoantigens or ROS, additional radiation (which may be re-aimed if it is believed that the target might have been missed) may be warranted or treatment plan adapted for greater therapeutic outcome.

Figure 10:
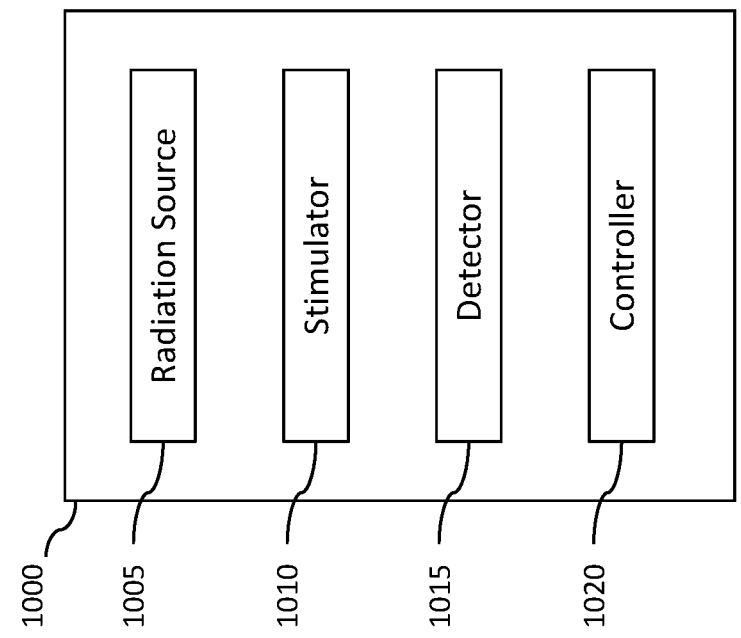
FIG. 10 depicts an exemplary radiotherapy system which may be used with exemplary NP payloads.

Referring to FIG. 10, an exemplary system 1000 may include a source of ionizing radiation 1005. This may be, for example, a source of x-rays, gamma rays, electrons, protons, etc. The source 1005 may be capable of emitting one or multiple radiation beams at a target. A stimulator 1010, capable of emitting, for example, electromagnetic or sound waves, may be included if polymer that is remotely activatable may be used. A detector 1015 may be included to detect emissions from the vicinity of the target site. The detector 105 may be an imaging system, such as an optical imaging system, that is capable of detecting signals resulting from interaction of functionalized NPs with proteins or antigens generated in the tumor microenvironment due to the irradiation or enhanced damage from Cerenkov radiation. A controller 1020 may include a processor and memory with instructions executable by the processor. The controller would function to control the radiation source and stimulator (e.g., timing and intensity of emissions), as well as the detector and evaluation of readings therefrom.

The present disclosure has described one or more preferred embodiments, and it should be appreciated that many equivalents, alternatives, variations, and modifications, aside from those expressly stated, are possible and within the scope of the invention.

The invention claimed is:

1. A radiation therapy method comprising:
   administering a payload comprising first high z nanoparticles (NPs) and second semiconductor NPs to a tissue site of a subject; and
   applying an ionizing first radiation directed at the site at which the payload was administered;
   wherein a second radiation is generated via interaction of the first high z NPs with the first radiation;
   wherein chemical species are generated via interaction of the second semiconductor NPs with the second radiation;
   wherein the chemical species are damaging to one or more cells at the tissue site, and
   wherein the first high z NPs include NPs selected from the group consisting of gold NPs, gadolinium NPs, and iron oxide NPs.

2. The method of claim 1, wherein the second semiconductor NPs are metal oxide NPs.

3. The method of claim 2, wherein the second semiconductor NPs include NPs selected from the group consisting of titanium oxide and zinc oxide.

4. The method of claim 1, wherein the second semiconductor NPs are doped with an image contrast agent.

5. The method of claim 1, wherein the first high z NPs emit electrons via photoelectric interaction with the first radiation.

6. The method of claim 5, wherein the electrons are damaging to one or more cells at the site.

7. The method of claim 1, wherein the first radiation is x-radiation.

8. The method of claim 1, wherein the second radiation is Cerenkov radiation.

9. The method of claim 8, wherein the first high z NPs emit electrons via photoelectric interaction with the first radiation, and wherein the Cerenkov radiation is generated via interaction of the electrons with tissue of the subject.

10. The method of claim 1, wherein the payload is administered via injection.

11. The method of claim 1, wherein the payload is administered via a radiotherapy (RT) device.

12. The method of claim 11, wherein the RT device includes a device selected from the group consisting of a fiducial marker, a radiotherapy spacer, and a radiotherapy beacon.

13. The method of claim 11, wherein the RT device includes a hollow core.

14. The method of claim 13, wherein at least a portion of the payload is situated in the hollow core.

15. The method of claim 11, wherein the RT device includes a polymer matrix.

16. The method of claim 15, wherein the polymer matrix includes a polymer selected from the group consisting of PLGA and chitosan.

17. The method of claim 15, wherein the polymer matrix is biodegradable, wherein the RT device releases at least a portion of the payload via biodegradation of the polymer matrix, and wherein biodegradation of the polymer matrix is remotely activated by a stimulator.

18. The method of claim 1, wherein the first radiation is delivered via a local radiation source comprising an implanted x-ray emitting radioisotope.

19. The method of claim 1, wherein the first radiation is delivered via external beam radiotherapy (EBRT).

20. The method of claim 1, wherein the payload further includes one or more immunologic adjuvants.

21. The method of claim 1, wherein the chemical species are reactive oxygen species (ROS).

22. A radiation therapy method comprising:
   administering a payload comprising high z nanoparticles (NPs) and semiconductor NPs to a tissue site of a subject; and
   applying a megavolt ionizing radiation directed at the site at which the payload was administered via an external radiation beam;
   wherein a Cerenkov radiation is generated via interaction of the megavolt ionizing radiation with the high z NPs at the tissue site;
   wherein chemical species are generated via interaction of the semiconductor NPs with the Cerenkov radiation;
   wherein the chemical species are damaging to one or more cells at the tissue site, and
   wherein the high z NPs include NPs selected from the group consisting of gold NPs gadolinium NPs, and iron oxide NPs.

23. The method of claim 22, wherein the semiconductor NPs include NPs selected from the group consisting of titanium oxide and zinc oxide.

24. The method of claim 22, wherein the payload further includes an immunologic adjuvant.

25. The method of claim 22, wherein the chemical species are reactive oxygen species generated via interaction of the semiconductor NPs with the Cerenkov radiation.

* * * * *